United States Patent
Matsui et al.

[11] Patent Number: 5,850,467
[45] Date of Patent: Dec. 15, 1998

[54] IMAGE DATA INSPECTING METHOD AND APPARATUS PROVIDING FOR EQUAL SIZING OF FIRST AND SECOND IMAGE DATA TO BE COMPARED

[75] Inventors: Shogo Matsui; Kenichi Kobayashi, both of Kawasaki, Japan

[73] Assignee: Fujitsu Limited, Kawasaki, Japan

[21] Appl. No.: 341,031

[22] Filed: Nov. 15, 1994

Related U.S. Application Data

[63] Continuation of Ser. No. 235,229, Apr. 29, 1994, abandoned, which is a continuation of Ser. No. 787,819, Nov. 5, 1991, abandoned.

[30] Foreign Application Priority Data

Nov. 5, 1990 [JP] Japan ................................ 2-299481

[51] Int. Cl.⁶ ..................................................... G06K 9/00
[52] U.S. Cl. ........................................................ 382/145
[58] Field of Search ............................. 382/1, 8, 30, 34, 382/48; 348/86, 92, 94, 95; G06K 9/00, 9/20, 9/62, 9/68; H04N 7/00

[56] References Cited

U.S. PATENT DOCUMENTS

| | | | |
|---|---|---|---|
| 4,797,939 | 1/1989 | Hoki et al. | 382/8 |
| 4,809,341 | 2/1989 | Matsui et al. | 382/8 |
| 4,853,967 | 8/1989 | Mandeville | 382/8 |
| 5,144,681 | 9/1992 | Kitakado et al. | 382/8 |
| 5,146,509 | 9/1992 | Hara et al. | 382/8 |

FOREIGN PATENT DOCUMENTS

| | | | |
|---|---|---|---|
| 61-108134 | 11/1984 | Japan | H01L 21/30 |
| 61-241996 | 10/1986 | Japan | H05K 3/00 |
| 2-170279 | 12/1988 | Japan | G06F 15/62 |
| 90-1976 | 3/1990 | Rep. of Korea | G06K 9/00 |
| 84/03784 | 9/1984 | WIPO . | |

OTHER PUBLICATIONS

Patent Abstracts of Japan, vol. 11, No. 100 (P–561), Mar. 28, 1987 & JP–A–61 251705 (Sumitomo Metal Ind Ltd), Nov. 8, 1986.

*Primary Examiner*—Jose L. Couso
*Attorney, Agent, or Firm*—Staas & Halsey

[57] ABSTRACT

An image data inspecting method detects whether or not a pattern described by a first image data and a pattern described by a second image data match. This method includes the steps of (a) carrying out a sizing process on the first and second image data so that the patterns described thereby are at least enlarged or reduced by the same amount, and (b) comparing the first and second image data which are processed in the step (a) to determine whether or not the processed first and second image data match.

8 Claims, 6 Drawing Sheets

IMAGE DATA INSPECTING METHOD AND APPARATUS PROVIDING FOR EQUAL SIZING OF FIRST AND SECOND IMAGE DATA TO BE COMPARED

This application is a continuation, of application Ser. No. 08/235,229, filed Apr. 29, 1994, now abandoned, which application is a continuation, of application Ser. No. 07/787, 819, filed Nov. 5, 1991, now abandoned.

BACKGROUND OF THE INVENTION

The present invention generally relates to image data inspecting methods and apparatuses, and more particularly to an image data inspecting method for inspecting whether or not two image data related to a pattern of a solid state electronic device, such as a semiconductor device, match, and an image data inspecting apparatus which employs such an image data inspecting method.

When producing a solid state electronic device such as a semiconductor device, photomasks and reticles are made to form patterns of each layer of the electronic device. Even if an extremely small defect exists in the patterns of such photomasks and reticles, the defect would greatly affect the product production. For this reason, the patterns of the photomasks and reticles are inspected upon completion in order to check the accuracy of the patterns.

Generally, the patterns of the photomask or reticle are converted into an electrical signal, that is, an image data, when making the above described inspection. This image data is compared or collated with an image data which is made in advance at the designing stage. This comparison is made to determine whether or not the two image data match for all regions of the photomask or reticle, and it is necessary that the two image data match in their entirety when this inspection is made.

Figure 1:
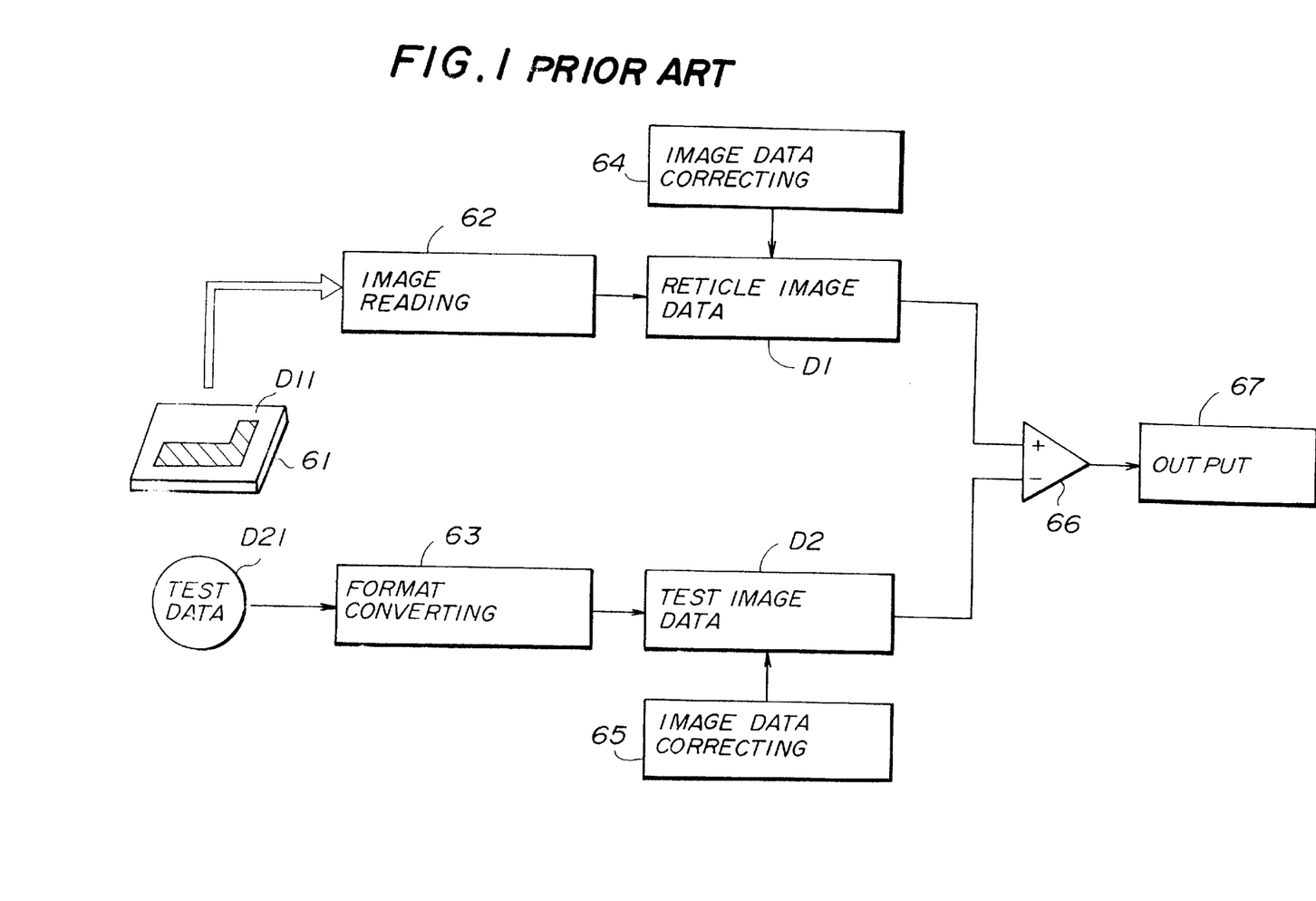
FIG. 1 is a system block diagram for explaining an example of a conventional reticle image inspecting method.

A description will be given of an example of a conventional reticle image inspecting method, by referring to FIG. 1. In FIG. 1, a pattern D11 which is formed on a reticle 61 by a metal thin film is converted into an electrical signal by an image reading part 62. The image reading part 62 is made up of an optical device which emits a reading light and a photoelectric conversion device which receives the reading light which is transmitted through the reticle pattern, for example. The image reading part 62 outputs a reticle image data D1 as the electrical signal.

For example, the entire region of the reticle is divided into units of the photoelectric conversion device, and the reticle image data D1 describes the pattern for each unit region. The signal format of the reticle image data D1 is such that the pattern is described by defining a center point coordinate (X1, Y1), a width (W1) and a height (H1) of the pattern.

A test data D21 is formed, prior to the production of the reticle, from design mask data, similarly to the exposure data which is formed for the reticle production. The signal format of the test image data D21 is such that the pattern existing with the entire reticle is described by defining a center point coordinate (X2, Y2), a width (W2) and a height (H2) of the pattern. Accordingly, the signal formats of the test data D21 and the reticle image data D1 are different, and a format converting part 63 is provided to convert the signal format of the test data D21 to match the signal format of the reticle image data D1. The format converting part 63 converts the test data D21 into a test image data D2.

A comparator part 66 compares the two image data D1 and D2, and outputs a detection signal which indicates whether or not the two image data D1 and D2 match. This detection signal is supplied to an output part 67. When the detection signal indicates that the two image data D1 and D2 match, this indicates that the inspected reticle is in satisfactory condition free of defects. On the other hand, when the detection signal indicates that the two image data D1 and D2 do not match, this indicates that the inspected reticle includes a defect. For the sake of convenience, the detection signal which indicates that the two image data D1 and D2 match will be referred to as a first detection signal, and the detection signal which indicates that the two image data D1 and D2 do not match will be referred to as a second detection signal.

The image data D1 and D2 may require correction if a modification or the like is made after the image data D1 and D2 are formed. In such a case, image data correcting parts 64 and 65 carry out corrections on the respective image data D1 and D2, such as correcting the rounding of the corner of the image.

The comparison of the two image data D1 and D2 corresponds to the process of continuously scanning to determine whether or not the center point coordinate, the width and the height of each pattern match between the two image data D1 and D2 for the entire region of the reticle on the X and Y coordinates, for example. Accordingly, it is necessary to scan all coordinate points on the entire region of the reticle, and the comparison at the comparator part 66 accordingly is carried out at an extremely high speed.

When a defect exists in the reticle and this defect is extremely small and is caused by a defective etching or the like, the second detection signal which indicates that the two image data D1 and D2 do not match lasts only for an extremely short time during the scan. However, since the comparator part 66 carries out the comparison at high speed, the scan frequency is extremely high. For this reason, there is a problem in that it is difficult to distinguish the second detection signal which lasts for the extremely short time due to the existence of the extremely small defect and a noise signal which is caused by a distortion in the signal waveform due to the high frequency.

If the detection sensitivity of the comparator part 66 is increased, the noise signal will simply be detected as the second detection signal, that is, the existence of a defect in the reticle. On the other hand, if the detection sensitivity of the comparator part 66 is decreased, it becomes impossible to detect an extremely small defect in the reticle. Generally, these problems always occur in the image data inspecting method and apparatus which inspect the matching state of the two image data by comparison.

SUMMARY OF THE INVENTION

Accordingly, it is a general object of the present invention to provide a novel and useful image data inspecting method and apparatus in which the problems described above are eliminated.

Another and more specific object of the present invention is to provide an image data inspecting method for detecting whether or not a pattern described by a first image data and a pattern described by a second image data match, comprising the steps of (a) carrying out a sizing process on the first and second image data so that the patterns described thereby are at least enlarged or reduced by the same amount, and (b) comparing the first and second image data which are processed in the step (a) to determine whether or not the processed first and second image data match. According to the image data inspecting method of the present invention, it is possible to easily detect an extremely small difference between the two image data even when a high speed scan is made during the inspection, without the need to specially improve the sensitivity of a comparator part which makes the comparison.

Still another object of the present invention is to provide an image data inspecting apparatus for detecting whether or not a pattern described by a first image data and a pattern described by a second image data match, comprising processing means for carrying out a sizing process on the first and second image data which are read from the memory means so that the patterns described thereby are at least enlarged or reduced by the same amount, memory means, coupled to the processing means, for storing processed first and second image data which are processed in the processing means, comparator means, coupled to the memory means, for comparing the processed first and second image data which are read from the memory means to determine whether or not the processed first and second image data match, and output means, coupled to the comparator means, for outputting a result of the comparison in the comparator means. According to the image data inspecting apparatus of the present invention, it is possible to easily detect an extremely small difference between the two image data even when a high speed scan is made during the inspection, without the need to specially improve the sensitivity of the comparator means.

Other objects and further features of the present invention will be apparent from the following detailed description when read in conjunction with the accompanying drawings.

DESCRIPTION OF THE PREFERRED EMBODIMENTS

Figure 2:
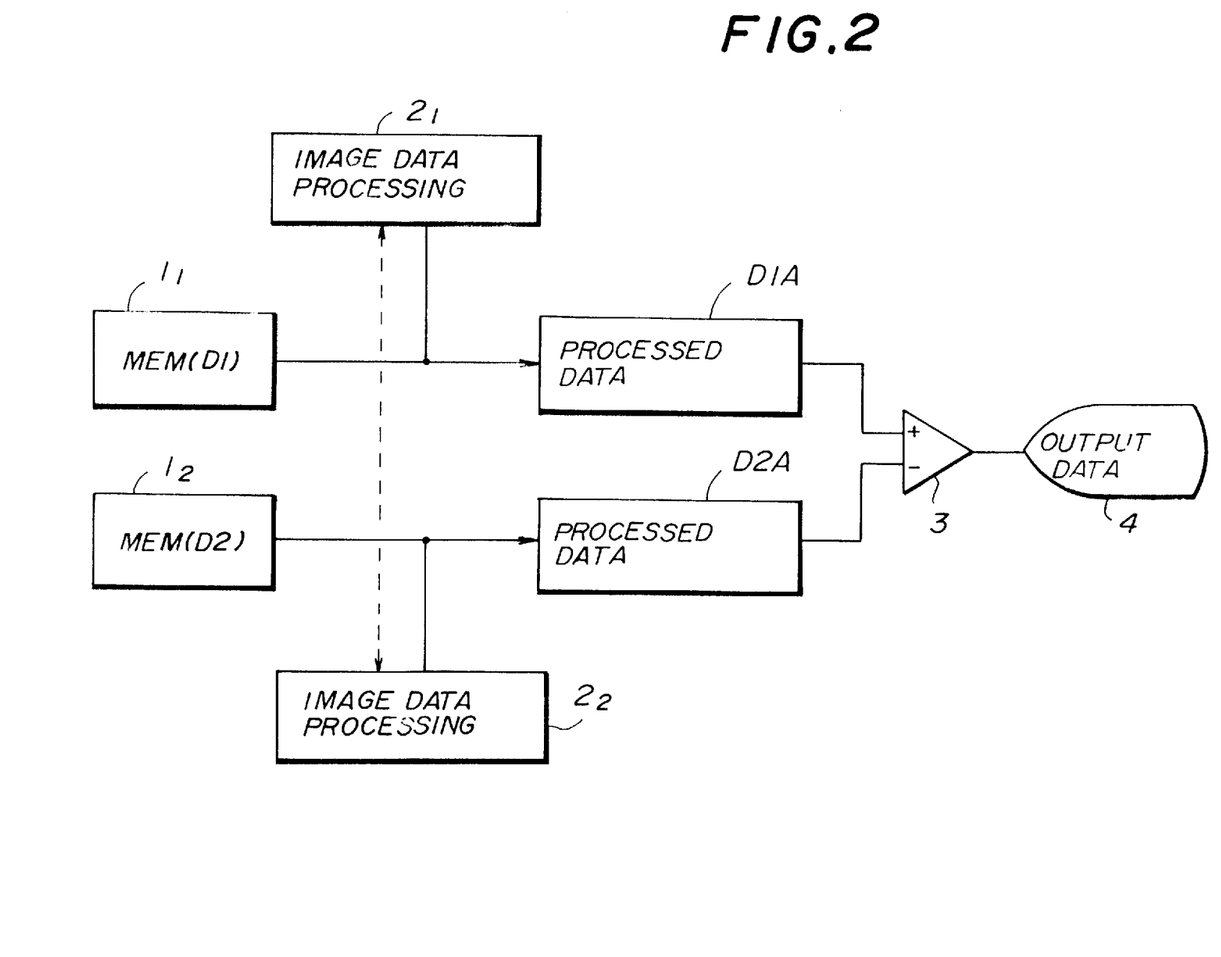
FIG. 2 is a system block diagram for explaining the operating principle of the present invention.

First, a description will be given of the operating principle of the present invention, by referring to FIG. 2.

In the present invention, first and second image data D1 and D2, which respectively describe a pattern, are compared to detect whether or not the patterns match. The first image data D1 is stored in a memory $1_1$, and the second image data D2 is stored in a memory $1_2$. An image data processing part $2_1$ processes the first image data D1 so that all patterns described by the first image data D1 are enlarged or reduced by the same amount, and an image data processing part $2_2$ processes the second image data D2 so that all patterns described by the second image data D2 are enlarged or reduced by the same amount. Hence, the first and second image data D1 and D2 are enlarged or reduced by the same amount and respectively formed into a first processed image data D1A and a second processed image data D2A. The above image data processing is also referred to as a sizing process. A comparator part 3 compares the first and second processed image data D1A and D2A so as to detect whether or not the two described images match. A comparison result output from the comparator part 3 is supplied to an output part 4.

According to the conventional method and apparatus of FIG. 1, the image data correcting parts 64 and 65 simply operate independently of each other, depending on the modifications to be made of the image data. However, in the present invention, the operations of the two image data processing parts $2_1$ and $2_2$, which likewise function prior to the image data comparison, are controlled and linked so that the same image data processing is carried out with respect to the two image data D1 and D2. The two image data D1 and D2 are enlarged or reduced so as to facilitate the determination of whether or not the two image data D1 and D2 match. In other words, the image data processing carried out in each of the image data processing parts $2_1$ and $2_2$ is an enlargement or reduction of the existing patterns. In this case, the conventional image data correcting part may be used as the image data processing part $2_1$ or $2_2$.

Because all patterns described by the two image data D1 and D2 are enlarged or reduced by the same amount, the difference between the two image data D1 and D2 is enlarged by the enlargement or reduction of the patterns. As a result, the second detection signal which is detected during the scan at the comparator part 3 lasts for a longer time when compared to the conventional method, and it is possible to detect that the two image data D1 and D2 do not match, with greater ease as compared to the conventional method.

Next, a description will be given of an embodiment of an image data inspecting method according to the present invention, by referring to FIG. 3. In this embodiment, the present invention is applied to the inspection of a reticle.

Figure 3:
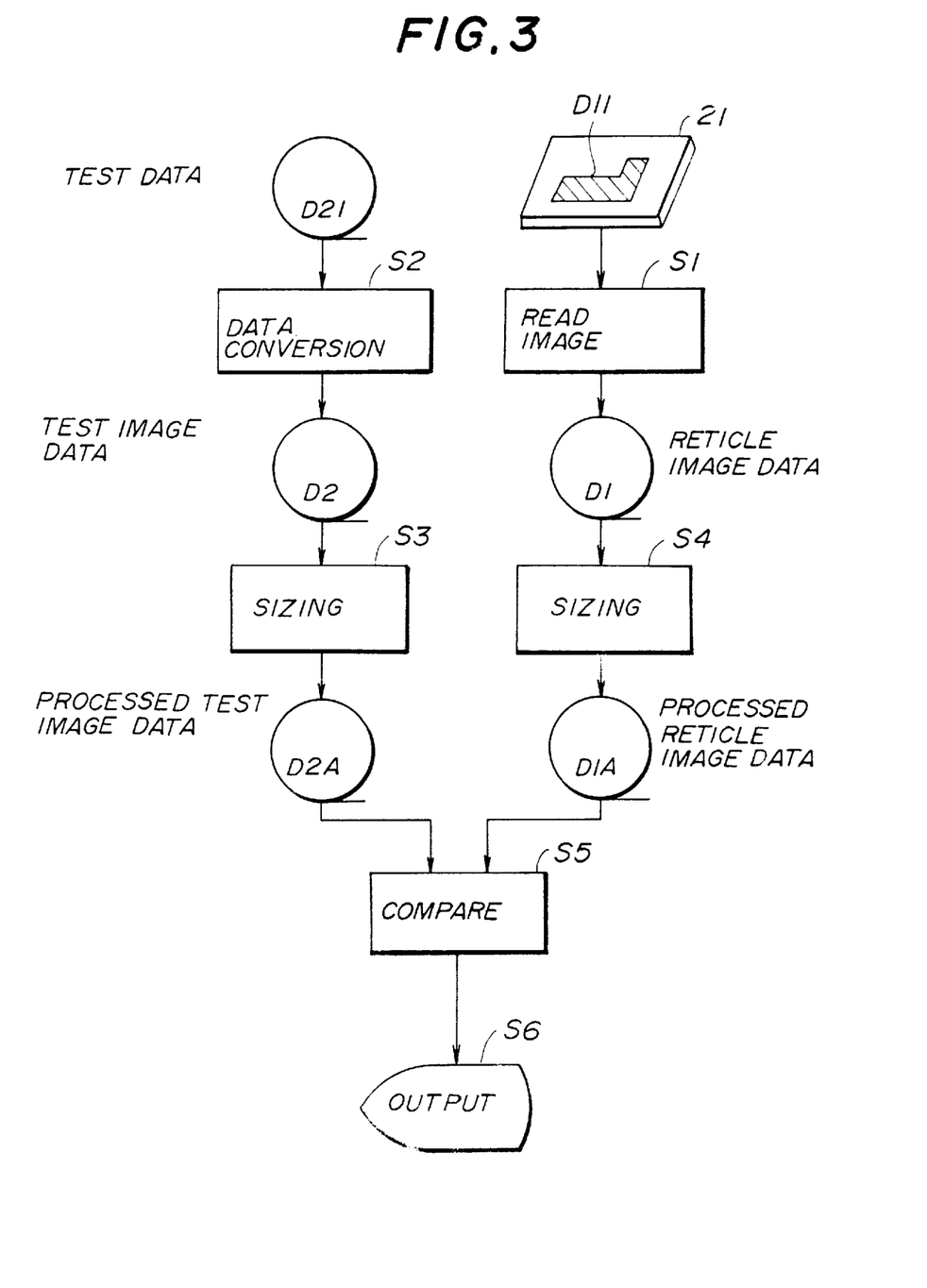
FIG. 3 is a flow chart for explaining an embodiment of an image data inspecting method according to the present invention.

In FIG. 3, a step S1 converts patterns D11 drawn on a reticle 21 into an electrical signal by use of a photoelectric conversion means such as an optical device and a charge coupled device (CCD), so as to read the pattern image. This electrical signal forms a first image data D1. On the other hand, a step S2 converts the format of a test data D21, which is prepared for use in inspecting the reticle 21, so that the format of a second image data D2 has the same format as the first image data D1. A step S3 enlarges or reduces the image data D2, and a step S4 enlarges or reduces the image data D1. The image data processing at the steps S3 and S4 is controlled so that the enlargement or reduction is made for the same amount. The steps S3 and S4 may be carried out simultaneously by two independent image data processing means or carried out successively by a single image data processing means.

The "enlargement" process refers to the process of enlarging all of the patterns described by the image data by moving each pattern contour to the outside and enlarging each pattern. The amount of the enlargement need not be the same for each direction. On the X-Y coordinate system, for example, a pattern having a width W and a height H may be enlarged by enlarging only the width W in the X direction or enlarging the width W in only the positive X direction. The pattern may be enlarged by enlarging the width W and the height H by a certain ratio. Further, the pattern may be enlarged by enlarging the width W and/or the height H by a constant amount. When detecting an extremely small defect, it is effective to enlarge the width W by a fixed amount in the X direction which is the scan direction, for example.

The "reduction" process refers to the process of reducing all of the patterns described by the image data by moving each pattern contour to the inside and reducing each pattern. In other words, the reduction process is a reverse process of the enlargement process, and the amount of the reduction need not be the same for each direction, as in the case of the enlargement.

Next, a description will be given of the enlargement process which is carried out with respect to the image data, by referring to FIGS. 4A through 4E.

Figure 4A:
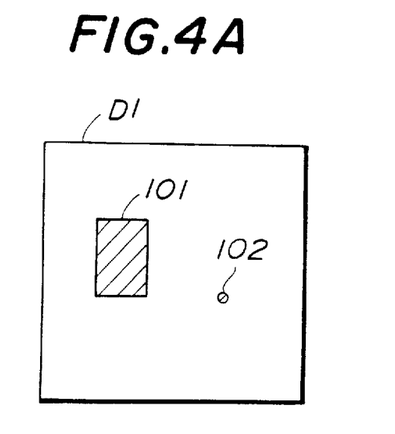
FIGS. 4A through 4E are diagrams for explaining an enlargement process.

In FIG. 4A, the reticle image data (first image data) D1 includes data related to a pattern 101 and an extremely small defect 102. When this reticle image data D1 is enlarged by the same constant amount in all directions, a processed reticle image data D1A shown in FIG. 4C is obtained. In the processed reticle image data D1A, the defect 102 is enlarged to a defect 112.

Figure 4B:
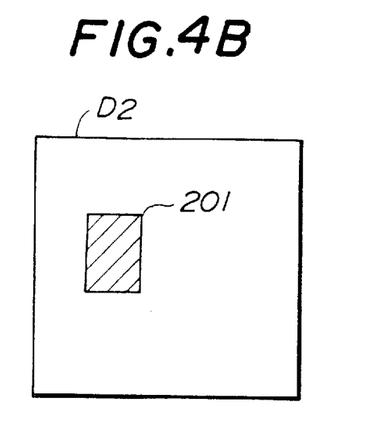
Figure 4C:
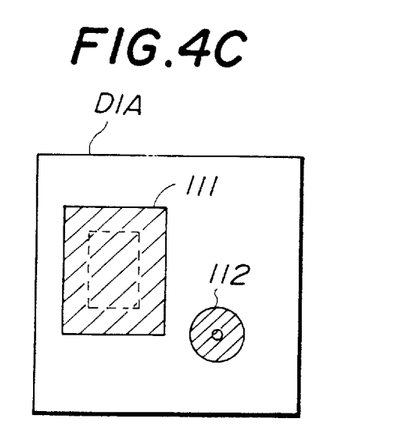
Figure 4D:
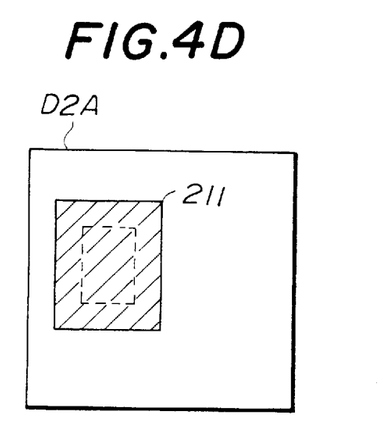

On the other hand, the test image data (second image data) D2 shown in FIG. 4B is also subjected to the same enlargement process and formed into a processed test image data D2A shown in FIG. 4D. The test image data D2 includes a pattern 201, and this pattern 201 is enlarged to a pattern 211 in the processed test image data D2A.

Figure 4E:
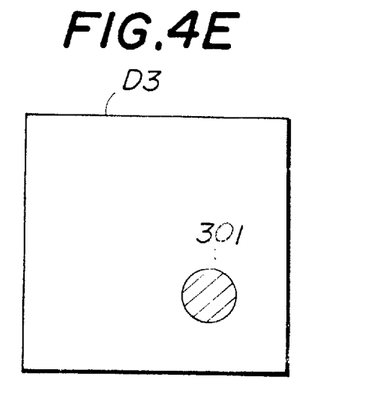

The two processed image data D1A and D2A are compared, and a compared output image data D3 shown in FIG. 4E is obtained as a result of the comparison. This compared output image data D3 includes a defect 301 which corresponds to the defect 102 and is enlarged with respect to the defect 102. In other words, the defect 301 corresponds to the enlarged difference between the two image data D1 and D2. Accordingly, the extremely small defect 102 in the reticle image data D1, which may not be found according to the conventional method depending on the detection sensitivity, can positively be detected as the defect 301 according to this embodiment. Hence, the reticle can be inspected with a high reliability, and the defect of the reticle can be found with a high accuracy.

If the reticle image data D1 shown in FIG. 4A were used to form a contact hole in a semiconductor device for interconnection purposes, for example, the pattern 101 is used as the contact hole. However, the existence of the defect 102 would form a contact hole where an interconnection should not be made. Hence, it may be seen that the elimination of the defect 102 is essential in such a case.

Next, a description will be given of the reduction process which is carried out with respect to the image data, by referring to FIGS. 5A and 5B.

Figure 5A:
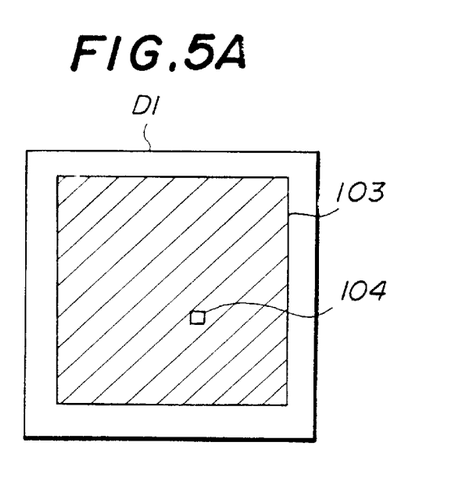
FIGS. 5A and 5B are diagrams for explaining a reduction process.
Figure 5B:
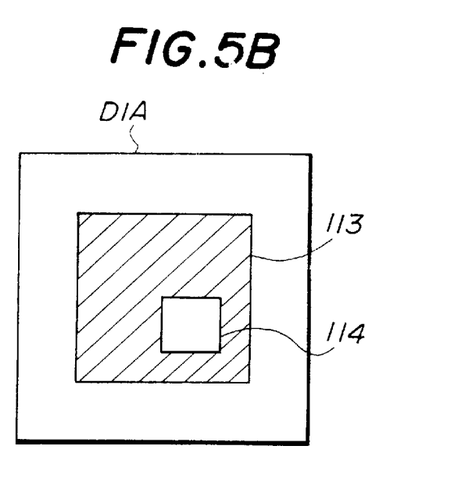

In FIG. 5A, the reticle image data (first image data) D1 includes data related to a pattern 103 and an extremely small defect 104. When this reticle image data D1 is reduced by the same constant amount in all directions, a processed reticle image data D1A shown in FIG. 5B is obtained. In the processed reticle image data D1A, the defect 104 is enlarged to a defect 114.

On the other hand, a test image data (second image data) D2 is also subjected to the same reduction process and formed into a processed test image data D2A. The test image data D2 includes a pattern but no defect, and this pattern is reduced in the processed test image data D2A.

The two processed image data D1A and D2A are compared, and a compared output image data D3 is obtained as a result of the comparison. This compared output image data D3 includes a defect which corresponds to the defect 104 and is enlarged with respect to the defect 104. In other words, the defect in the compared output image data D3 corresponds to the enlarged difference between the two image data D1 and D2. Accordingly, the extremely small defect 104 in the reticle image data D1, which may not be found according to the conventional method depending on the detection sensitivity, can positively be detected as the defect 301 according to this embodiment. Hence, the reticle can be inspected with a high reliability, and the defect of the reticle can be found with a high accuracy.

The reduction process is particularly effective in finding a defect when the pattern exists over a large region and the defect signal which is related to the extremely small defect in the reticle corresponds to a signal which describes an image in which no pattern exists.

If the reticle image data D1 shown in FIG. 5A were used to prevent formation of an impurity region when injecting impurities into layer of a semiconductor device, for example, the pattern 103 is used as the mask. However, the existence of the defect 104 would form an impurity region at a location where no impurity region should be formed. Hence, it may be seen that the elimination of the defect 104 is essential in such a case.

Returning to the description of FIG. 3, a step S5 compares the processed reticle image data D1A and the processed test image data D2A to determine whether or not the two image data match. A step S6 outputs the result of the comparison made in the step S6. For example, the result of the comparison is displayed on a display.

Next, a description will be given of an embodiment of an image data inspecting apparatus according to the present invention, by referring to FIG. 6.

Figure 6:
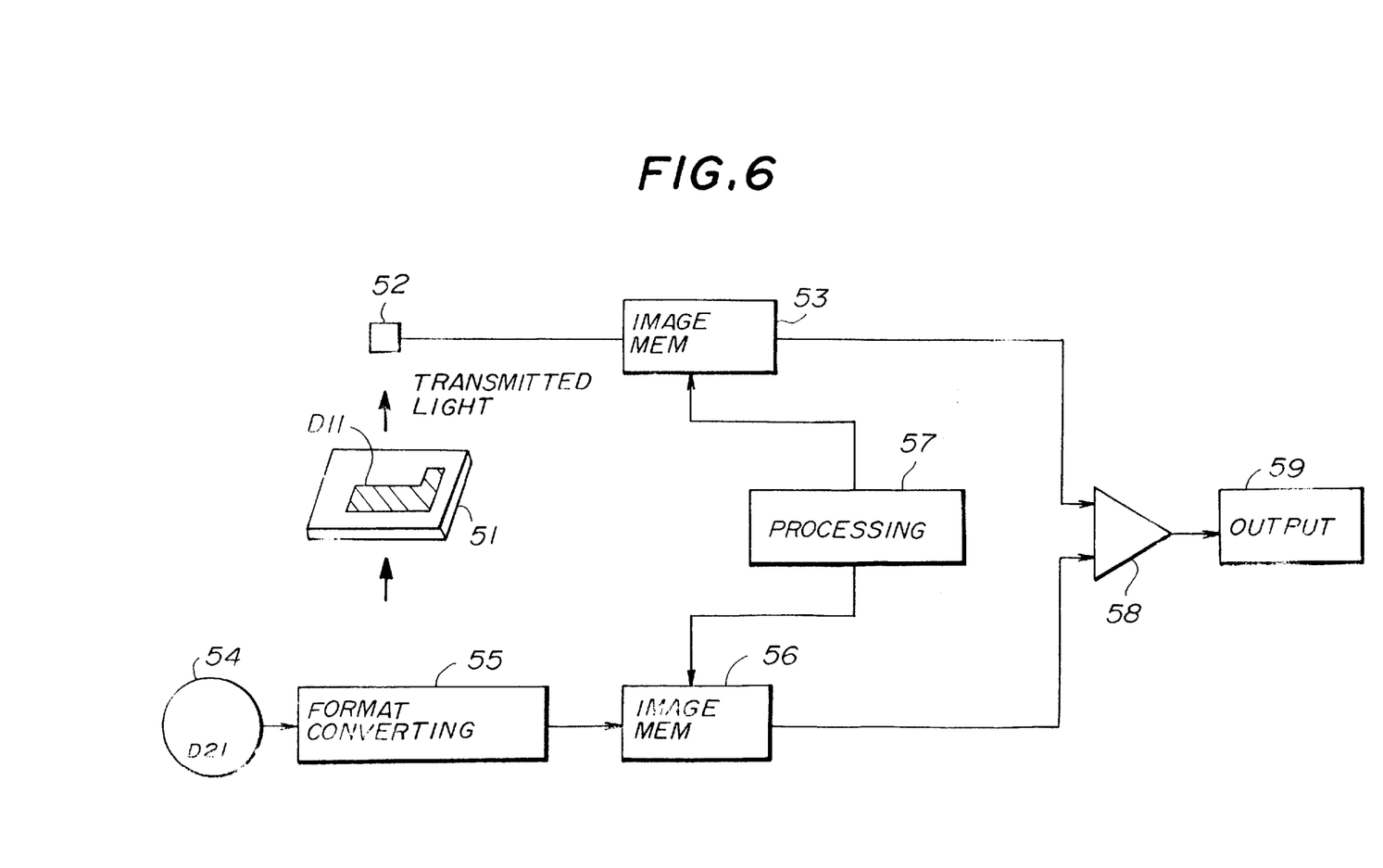
FIG. 6 is a system block diagram showing an embodiment of an image data inspecting apparatus according to the present invention.

In FIG. 6, a pattern D11 of a reticle 51 is read or scanned by an optical device (not shown) and a photoelectric conversion part 52, and the reticle image data which is thus read is stored in an image memory 53. On the other hand, a test image data D21 which is recorded on a magnetic tape 54 is reproduced and supplied to a format converting part 55. The format converting part 55 converts the signal format of the test image data D21 to a signal format identical to that of the reticle image data which is stored in the image memory 53. The test image data having the converted signal format is stored in an image memory 56.

An enlarge/reduce processing part 57 carries out an enlarging process or a reducing process with respect to the respective image data which are stored in the image memories 53 and 56. A processed reticle image data which is obtained as a result of the image processing in the enlarge/reduce processing part 57 is stored in the image memory 53, while a processed test image data which is obtained as a result of the image processing in the enlarge/reduce processing part 57 is stored in the image memory 56. The processed reticle image data read from the image memory 53 and the processed test image data read from the image memory 56 are supplied to a comparator part 58 and compared therein. A result of the comparison in the comparator part 58 is supplied to an output part 59 and displayed, for example. The result of the comparison which is displayed is as shown in FIG. 4E, for example, if the processed reticle image data and the processed test image data do not match.

The enlarging and reducing processes are further disclosed in a U.S. Pat. No. 4,809,341, the disclosure of which is hereby incorporated by reference. The enlarging and reducing processes are respectively referred to as "reduction" and "magnification" in this United States Patent.

Figure 7:
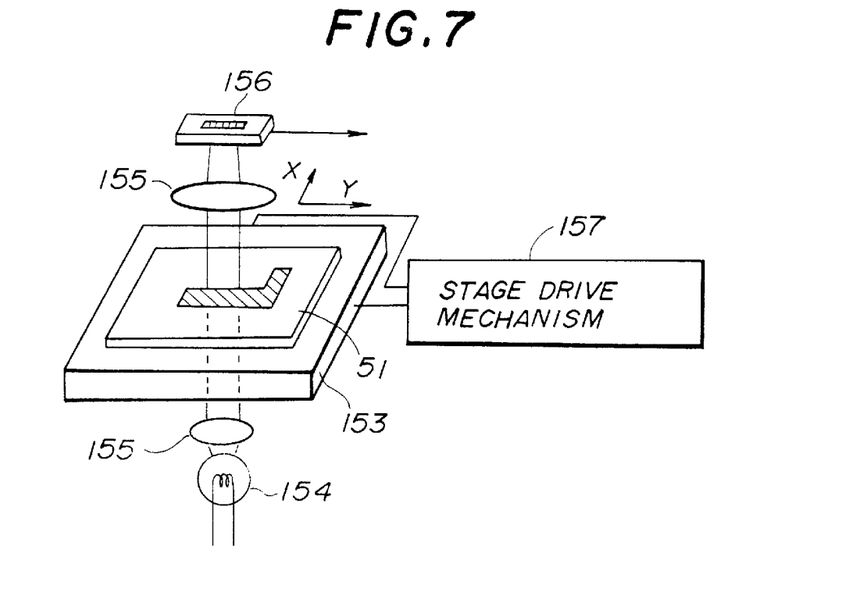
FIG. 7 is a diagram showing an embodiment of a reading part shown in FIG. 6.

FIG. 7 shows an embodiment of a reading part shown in FIG. 6. In FIG. 7, the reticle 51 is placed on a stage 153 and is irradiated from the back side by a light emitted from a light source 154. The light from the light source 154 is transmitted through the reticle 51 with the aid of lens systems 155, and the transmitted light is received by a sensor 156 which corresponds to the photoelectric conversion part 152 shown in FIG. 6. The stage 153 is moved by a stage drive mechanism 157 which may be controlled by a control unit (not shown) which controls the operation of the apparatus shown in FIG. 6. Hence, the reticle 51 on the stage 153 can be moved in X and Y directions.

For example, the sensor 156 includes a one dimensional charge coupled device (CCD) having 1024 detecting elements linearly arrayed. In this embodiment, the sensor 156 scans a distance of 1 mm in the X direction and detects the reticle surface of 1 mm length along the Y direction. As a result, an area of 1 mm$^2$ on an object surface is resolved into 1024×1024 bit data and this data is stored in the image memory 53 shown in FIG. 6.

In the above described case, 1 bit of the data represents whether or not the pattern exists in an area of about 1 $\mu$m$^2$. The object area represented by each bit of data varies depending on a magnifying ratio of the lens systems 155, and therefore, it is possible to inspect the reticle 51 by changing only the magnification ratio of the lens systems 155.

In the embodiments described above, the present invention is applied to the inspection of the reticle image. However, the present invention is applicable to any type of inspection which requires comparison of two image data to determine whether or not the two image data match. For example, the present invention is also applicable to the collating of a mask data with a test data, inspection of a wafer, a semiconductor chip and the like, and comparison of two identical chips. When comparing two identical chips, the image data of the two chip patterns which are obtained via the optical device and the photoelectric conversion device are stored in image memories, and, after enlarging or reducing the two image data, a comparator part compares the two processed image data to determine whether or not the two image data match. Hence, it is possible to inspect the sameness of the two chips with ease.

In addition, in the above described embodiments, each image data describes the reticle pattern using the same signal format. However, the image data does not necessarily have to use the same signal format. In other words, the image data related to the reticle normally describes the reticle pattern using a signal format such that the region of the reticle is divided into a plurality of small regions and the reticle pattern is described in terms of the small regions. In this case, the signal format of the reticle image data may or may not be converted into the signal format identical to that of the test image data, because the comparator part may be provided with a function of carrying out predetermined processes corresponding to the enlarging or reducing process on the two image data having mutually different signal formats when making the comparison.

In the described embodiments, the enlarging or reducing process is carried out once with respect to the two image data which are compared. However, in order to improve the accuracy with which the two image data are collated, it is possible to make one comparison after enlarging the two image data and to make another comparison after reducing the two image data, so as to ensure enlargement of the difference between the two compared image data if any.

Further, the present invention is not limited to these embodiments, but various variations and modifications may be made without departing from the scope of the present invention.

What is claimed is:

1. A image data inspecting method, comprising:

storing in a memory first image data of a first actual pattern obtained by optically imaging an actual element selected from among a reticle, a mask, a wafer and a chip and second image data of a second pattern comprising a test pattern and obtained from storage;

sizing, with the aid of an image data processor, the first and second image data by a same amount;

comparing, using a comparator, the sized first and second image data to determine whether the sized first and second image data match; and based upon the determination of the comparing step, correspondingly concluding whether the first pattern matches the second pattern wherein:

the sizing step includes a step of enlarging and a step of reducing the first and second image data; and the comparing step includes a first step of comparing the enlarged first and second image data and making a first determination whether Or not the enlarged first and second image data match and a second step of comparing the reduced first and second image data and making a second determination of whether or not the reduced first and second image data match; and the concluding steps based upon the first and second determinations made by the comparing step.

2. The image data inspecting method as claimed in claim 1, wherein:

the sizing step includes a step of enlarging and a step of reducing the first and second image data; and the comparing step includes a first step of comparing the enlarged first and second image data and making a first determination whether or not the enlarged first and second image data match and a second step of comparing the reduced first and second image data and making a second determination of whether or not the reduced first and second image data match; and the concluding step is based upon the first and second determinations made by the comparing step.

3. The image data inspecting method as claimed in claim 1, wherein the first and second image data have respective first and second signal formats and which further comprises the step of converting one of the first and second signal formats of the respective first and second image data so that the first and second signal formats of the respective first and second image data are the same, prior to performing the comparing step.

4. The image data inspecting method as claimed in claim 1, which further comprises the step of displaying the determination of the comparing step.

5. An image data inspecting apparatus, comprising:

first means for providing first image data of a first actual pattern obtained by optically imaging an actual element from among a reticle, a mask, a wafer and a chip;

second means for providing second image data of a second pattern comprising a test pattern obtained from storage;

processing means for sizing the first and second image data by a same amount;

memory means, coupled to said processing means, for storing the sized first and second image data;

comparator means, coupled to said memory means, for receiving from the memory means and comparing the sized first and second image data to determine whether the sized first and second image data match; and output means, coupled to said comparator means, for outputting a determination of said comparator means wherein:

said processing means sizes the first and second image data by selectively and separately, enlarging the first and second image data by the same amount and reducing the first and second image data by the same amount; and said comparator means separately and in a first step compares the enlarged first and second image data to make a first determination whether or not the enlarged first and second image data match and, in a second step, compares the reduced first and second image data to make a second determination whether or not the reduced first and second image data match.

6. The image data inspecting apparatus as claimed in claim 5, wherein:

said processing means sizes the first and second image data by, selectively and separately, enlarging the first and second image data by the same amount and reducing the first and second image data by the same amount; and said comparator means, separately and in a first step, compares the enlarged first and second image data to make a first determination whether or not the enlarged first and second image data match and, in a second step, compares the reduced first and second image data to make a second determination whether or not the reduced first and second image data match.

7. The image data inspecting apparatus as claimed in claim 5 wherein the first and second image data have respective first and second signal formats, further comprising converting means, coupled to said memory means, for converting one of the first and second signal formats of the respective first and second image data so that the first and second signal formats of the respective first and second image data are the same signal format when the sized first and second image data are compared by said comparator means.

8. The image data inspecting apparatus as claimed in claim 5, wherein said output means displays the result of the determination of said comparator means.

\* \* \* \* \*

UNITED STATES PATENT AND TRADEMARK OFFICE
CERTIFICATE OF CORRECTION

PATENT NO. : 5,850,467
DATED : December 15, 1998
INVENTOR(S) : Shogo MATSUI et al It is certified that error appears in the above-identified patent and that said Letters Patent is hereby corrected as shown below:

Col. 8,   line 21, change "Or" to --or--.

Col. 9,   line 9, after "step" insert --,--.

Signed and Sealed this

Third Day of August, 1999

Attest:

Q. TODD DICKINSON

Attesting Officer          Acting Commissioner of Patents and Trademarks